United States Patent [19]

Trombetta et al.

[11] Patent Number: 5,603,707
[45] Date of Patent: Feb. 18, 1997

[54] ABSORBENT ARTICLE HAVING A REWET BARRIER

[75] Inventors: Liberatore A. Trombetta, Hamilton; Dhanraj S. Patel, Mississauga; Dennis A. Darby, Hamilton; Jayne S. Huhtanen, Toronto, all of Canada

[73] Assignee: The Procter & Gamble Company, Cincinnati, Ohio

[21] Appl. No.: 563,711

[22] Filed: Nov. 28, 1995

[51] Int. Cl.$^6$ .......................... A61F 13/15; A61F 13/20
[52] U.S. Cl. .......................... 604/383; 604/370; 604/378
[58] Field of Search .................................. 604/358, 370, 604/378, 381, 383, 385.1

[56] References Cited

U.S. PATENT DOCUMENTS

| | | |
|---|---|---|
| 3,927,673 | 12/1975 | Taylor . |
| 3,929,135 | 12/1975 | Thompson . |
| 3,945,386 | 3/1976 | Anczurowski et al. ................ 604/370 |
| 3,994,299 | 11/1976 | Karami . |
| 4,321,924 | 3/1982 | Ahr ........................................ 604/370 |
| 4,323,069 | 4/1982 | Ahr et al. . |
| 4,324,246 | 4/1982 | Mullane et al. ........................ 604/370 |
| 4,341,217 | 7/1982 | Ferguson et al. . |
| 4,342,314 | 8/1982 | Radel et al. . |
| 4,463,045 | 7/1984 | Ahr et al. . |
| 4,637,819 | 1/1987 | Ouellette et al. . |
| 4,726,976 | 2/1988 | Karami et al. . |
| 5,171,238 | 12/1992 | Kajander . |
| 5,342,334 | 8/1994 | Thompson et al. ..................... 604/378 |
| 5,352,217 | 10/1994 | Curro ...................................... 604/378 |
| 5,368,910 | 11/1994 | Langdon ................................. 604/378 |

FOREIGN PATENT DOCUMENTS

| | | |
|---|---|---|
| 0523719A1 | 1/1993 | European Pat. Off. . |
| 0545423A1 | 6/1993 | European Pat. Off. . |
| 91/09583 | 7/1991 | WIPO . |
| 92/18078 | 10/1992 | WIPO . |
| 93/09741 | 5/1993 | WIPO . |

Primary Examiner—John G. Weiss
Assistant Examiner—P. Zuttarelli
Attorney, Agent, or Firm—Kevin C. Johnson; Steven W. Miller; Jacobus C. Rasser

[57] ABSTRACT

The present invention provides an absorbent article having a rewet barrier. The absorbent article includes a liquid pervious topsheet, a liquid impervious backsheet joined to the topsheet, an absorbent core positioned between the topsheet and the backsheet, a fibrous acquisition layer positioned between the topsheet and the absorbent core, and a rewet barrier positioned between the fibrous acquisition layer and the absorbent core. The rewet barrier is an apertured, macroscopically expanded, three-dimensional polymeric web having a body facing surface and a garment facing surface.

16 Claims, 2 Drawing Sheets

ABSORBENT ARTICLE HAVING A REWET BARRIER

FIELD OF THE INVENTION

The present invention relates to absorbent articles such as sanitary napkins, disposable diapers, incontinence briefs, incontinence pads, and the like, and more particularly, the present invention relates to absorbent articles having a rewet barrier.

BACKGROUND OF THE INVENTION

It has long been known in the disposable absorbent bandage art that it is extremely desirable to construct absorptive devices such as disposable diapers, catamenial pads, sanitary napkins, incontinence briefs, incontinence pads, and the like, which present a dry surface feel to the user to improve wearing comfort and to minimize the development of undesirable skin conditions due to prolonged exposure to moisture absorbed within the bandage. Accordingly, it is generally desirable to promote fluid transfer in a direction away from the wearer and into an absorbent element, while resisting fluid transfer in the reverse direction.

Conventional absorbent articles typically include an absorbent element (sometimes referred to as an absorbent core) interposed between a fluid pervious body-contacting element (sometimes referred to as a topsheet or an overwrap) and a fluid impervious protective barrier (sometimes referred to as a backsheet). The absorbent element is, of course, intended to receive and contain bodily fluids such as menses and urine. The body-contacting element is intended to provide more or less comfortable and dry-feeling contact with body surfaces while allowing free passage of fluids therethrough and into the absorbent element. The protective barrier-is intended to prevent bodily fluids which are expelled or which escape from the absorbent element s from soiling the user's garments.

The comfort of the user is enhanced if the absorbent article, in addition to its properties of high fluid transmisivity and fluid retention, exhibits the characteristic of uni-directional fluid transmisivity. This will improve what it known as the rewet characteristic of the absorbent product. Fluid should quickly and easily transmit through the topsheet and into the absorbent core. As the absorbent core becomes saturated, fluid will tend to pass back through the absorbent article, or rewet, causing user discomfort. As the absorbent core becomes increasingly saturated during use or is subjected to a pressure, there will be a tendency of the fluid to transmit back through the cover, or rewet the cover's surface and hence the body of the user. This discomfort caused by rewetting can impel the user to discard the absorbent product before its useful life has terminated. Therefore, it is desirable to inhibit such rewetting and to resultant user discomfort.

SUMMARY OF THE INVENTION

The present invention pertains, in a preferred embodiment, to an absorbent article, e.g., sanitary napkin, pantiliner, diaper, adult incontinence brief, incontinence pad, bandage, and the like, having a rewet barrier. The absorbent article comprises a liquid pervious topsheet, a liquid impervious backsheet joined to the topsheet, an absorbent core positioned between the topsheet and the backsheet, a fibrous acquisition layer positioned between the topsheet and the absorbent core, and a rewet barrier positioned between the fibrous acquisition layer and the absorbent core. The rewet barrier comprises an apertured, macroscopically expanded, three-dimensional, polymeric web having a body facing surface and a garment facing surface.

In another embodiment, the absorbent article includes a second fibrous acquisition layer positioned between the rewet barrier and the absorbent core.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify identical elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
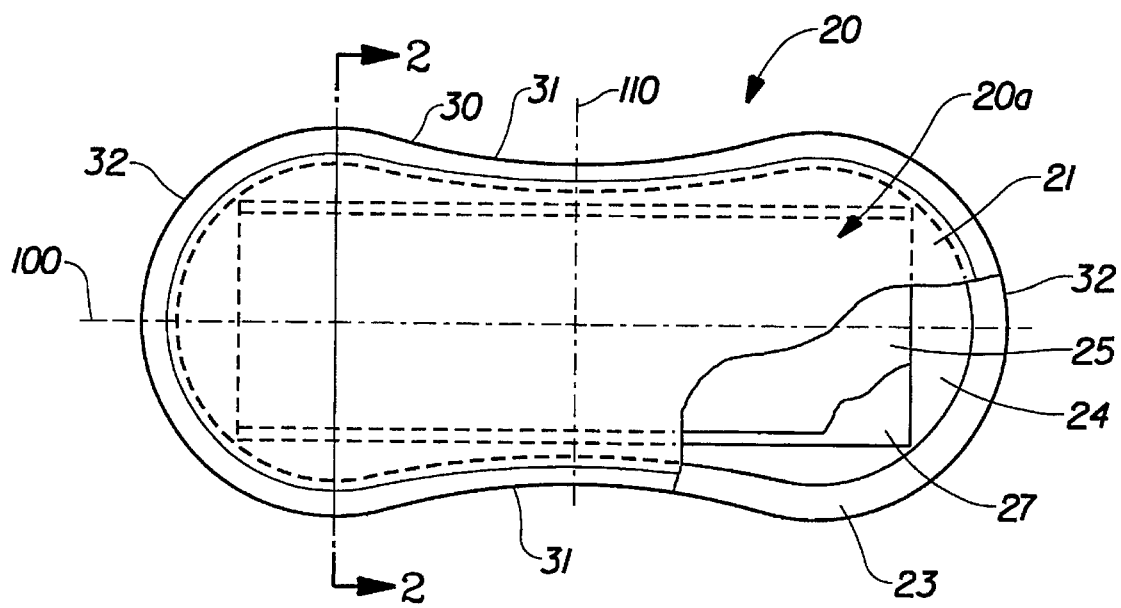
FIG. 1 is a top plan view of an incontinence pad with portions cut-away to more clearly show the construction of the incontinence pad.

A preferred embodiment of a unitary disposable absorbent article of the present invention is the incontinence pad 20 shown in FIG. 1. It should be understood, however, that the present invention is also applicable to other absorbent articles such as sanitary napkins, disposable diapers, incontinence briefs, training pants and the like.

FIG. 1 is a plan view of the incontinence pad 20 of the present invention in its flat-out state with portions of the structure being cut-away to more clearly show the construction of the incontinence pad 20 and with the portion of the incontinence pad 20 which faces or contacts the wearer, oriented towards the viewer. As shown in FIG. 1, the incontinence pad 20 preferably comprises a liquid pervious topsheet 21, a liquid impervious backsheet 23 joined with the topsheet 21, an absorbent core 24 positioned between the topsheet 21 and the backsheet 23, a fibrous acquisition layer 25 positioned between the topsheet 21 and the absorbent core 24, and a rewet barrier 27 positioned between the acquisition layer 25 and the absorbent core 24.

The incontinence pad 20 has two surfaces, a body-contacting surface or body facing surface 20a and a garment facing surface 20b. The incontinence pad 20 is shown in FIG. 1 as viewed from its body facing surface 20a. The body facing surface 20a is intended to be worn adjacent to the body of the wearer while the garment facing surface 20b is on the opposite side and is intended to be placed adjacent to the wearer's undergarments when the incontinence pad 20 is worn. The incontinence pad 20 has two centerlines, a longitudinal centerline 100 and a transverse centerline 110. The term "longitudinal", as used herein, refers to a line, axis or direction in the plane of the incontinence pad 20 that is generally aligned with (e.g., approximately parallel to) a vertical plane which bisects a standing wearer into lea and right body halves when the incontinence pad 20 is worn. The terms "transverse" or "lateral" as used herein, are interchangeable, and refer to a line, axis or direction which lies within the plane of the incontinence pad 20 that is generally perpendicular to the longitudinal direction. FIG. 1 also shows that the incontinence pad 20 has a periphery 30 which is defined by the outer edges of the incontinence pad 20 in which the longitudinal edges (or "side edges") are designated 3 1 and the end edges (or "ends") are designated 32.

FIG. 1 shows a preferred embodiment of the incontinence pad 20 in which the topsheet 21 and the backsheet 23 have length and width dimensions generally larger than those of the absorbent core 24. The topsheet 21 and the backsheet 23 extend beyond the edges of the absorbent core 24 to thereby form portions of the periphery.

Figure 2:
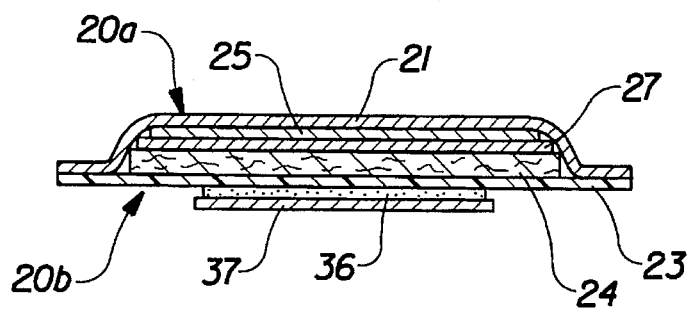
FIG. 2 is a cross-sectional view of the incontinence pad of FIG. 1 taken along section line 2—2.

FIG. 2 is a cross-sectional view of the incontinence pad 20 taken along section line 2—2 of FIG. 1. As can be seen in FIG. 2, the incontinence pad 20 preferably includes an adhesive fastening means 36 for attaching the incontinence pad 20 to the undergarment of the wearer. Removable release liners 37 cover the adhesive fastening means 36 to keep the adhesive from sticking to a surface other than a crotch portion of the undergarment prior to use.

The absorbent core 24 may be any absorbent means which is capable of absorbing or retaining liquids (e.g., menses and/or urine). As shown in FIGS. 1 and 2, the absorbent core 24 has a body facing surface, a garment facing surface, side edges, and end edges. The absorbent core 24 may be manufactured in a wide variety of sizes and shapes (e.g., rectangular, oval, hourglass, dog bone, asymmetric, etc.) and from a wide variety of liquid-absorbent materials commonly used in incontinence pads and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the incontinence pad. Further, the size and absorbent capacity of the absorbent core may be varied to accommodate different uses.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, The Procter & Gamble Company, published Oct. 22, 1986 in the name of Duenk, et al.; International Publication Number WO 94/28838, published Dec. 22, 1994 in the name of Palumbo, et al.; and International Publication Number WO 94/01069, published Jan. 20, 1994 in the name of Palumbo, et al. Each of these patents are incorporated herein by reference.

The backsheet 23 and topsheet 21 are positioned adjacent the garment facing surface and the body facing surface, respectively, of the absorbent core 24 and are preferably joined thereto and to each other by attachment means (not shown) such as those well known in the art. For example, the backsheet 23 and/or the topsheet 21 may be secured to each other or to other components by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 has a body facing surface and a garment facing surface. The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the incontinence pad 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P 18-0401 and by Tredegar Corporation, of Terre Haute, Ind., under the designation XP-39385. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

The topsheet 21 is compliant, soft feeling, and non-irritating to the wearer's skin. Further, the topsheet is liquid pervious permitting liquids (e.g., menses and/or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic film; and thermoplastic scrims. Suitable woven and nonwoven materials can be comprised of natural fibers (e.g., wood or cotton fibers), synthetic fibers (e.g., polymeric fibers such as polyester, polypropylene, polyethylene fibers, or bicomponent fibers) or from a combination of natural and synthetic fibers. A preferred topsheet comprises an apertured formed film. Apertured formed films are preferred for the topsheets because they are pervious to body exudates and yet nonabsorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body facing surface of the formed film topsheet is hydrophilic so as to help liquid to transfer through the topsheet faster than if the body facing surface was not hydrophilic so as to diminish the likelihood that bodily fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body facing surface of the topsheet can be made hydrophilic by treating it with a surfactant such as is described in the above referenced U.S. Pat. No. 4,950,254 issued to Osborn, incorporated herein by reference.

Another suitable topsheet comprises two strips of nonwoven material secured to a formed film. The nonwoven strips are positioned along the longitudinal edges of the incontinence pad. In a preferred embodiment, the nonwoven material is hydrophobic. An example of a topsheet comprising nonwoven material secured to a formed film is described in International Publication Number WO 93/09744, The Procter & Gamble Company, published May 27, 1993 in the name of Sugahara et al. which is incorporated herein by reference.

Another suitable topsheet comprises an upper layer constituted by a nonwoven textile of synthetic fibers, an intermediate layer constituted by a film material, and a lower layer constituted by a nonwoven textile of synthetic fibers. An example of such a topsheet is described in U.S. Pat. No. 4,780,352 issued to Palumbo on Oct. 25, 1988, which is incorporated herein by reference.

The fibrous acquisition layer 25 can be of any desired shape. Suitable shapes include for example, circular, rectangular, triangular, trapezoidal, oblong, dog bone, hourglass, oval, asymmetric, etc. In the embodiment of the incontinence pad 20 shown in FIG. 1, the acquisition layer 25 has a rectangular shape. Further, the acquisition layer 25 has a length equal to that of the rewet barrier 27 and a width generally smaller than that of the rewet barrier 27. The fibrous acquisition layer 25 may have length and width dimensions generally larger or smaller than those of the rewet barrier 27.

The fibrous acquisition layer 25 may serve several functions including accepting a high rate of fluid intake, serving as a temporary reservoir for the fluid, improving the wicking of fluids over and into the absorbent core, and draining substantially completely into the absorbent core in order to remain empty for subsequent fluid loadings. There are several reasons why the improved wicking of bodily fluids is important, including providing a more even distribution of the bodily fluids throughout the absorbent core. The wicking referred to herein may encompass the transportation of liquids in one, two, or all directions (i.e., in the x-y plane and/or in the z-direction). In addition, this element must resist collapse when wet so that it maintains its performance through multiple loadings. This element must do all these things while also remaining thin.

The fibrous acquisition layer 25 may be comprised of several different materials including nonwoven or woven webs of synthetic fibers including polyester, polypropylene, or polyethylene; natural fibers including cotton or cellulose; blends of such fibers; or any equivalent materials or combinations of materials. Suitable nonwoven webs include bonded carded webs, spunbonded webs, meltblown webs, and thermally bonded airlaid webs. The acquisition layer may be joined with the topsheet and the rewet barrier by any of the conventional means for joining webs together such as adhesives, heat bonds, pressure bonds, ultrasonic bonds, dynamic mechanical bonds, or any other suitable attachment means or combinations of these attachment means as are known in the art.

If the fibrous acquisition layer 25 is a nonwoven web, the nonwoven web may be a spunbonded web, a meltblown web, a bonded carded web, or a thermally bonded airlaid web. The nonwoven web may be made of fiber forming polymers such as, for example, polyesters, polyamines, and polyolefins. Exemplary polyolefins include one or more of polypropylene, polyethylene, ethylene copolymers, propylene copolymers, and butene copolymers. In another embodiment, the acquisition layer may be a multilayer material having, for example, at least one layer of a spunbonded web joined to at least one layer of a meltblown web, a bonded carded web, a thermally bonded airlaid web, or other suitable material. Alternatively, the nonwoven web may be a single layer of material such as, for example, a spunbonded web or a meltblown web.

The nonwoven web may also be a composite made up of a mixture of two or more different fibers or a mixture of fibers and particles. Such mixtures may be formed by adding fibers and/or particulates to the gas stream in which the meltblown fibers or spunbonded fibers are carried so that an intimate entangled commingling of fibers and other materials, e.g., wood pulp, staple fibers, superabsorbent materials, and particles occurs prior to collection of the fibers.

In another preferred embodiment, the nonwoven web may be comprised of bicomponent fibers. The bicomponent fiber is preferably a thermobondable bicomponent fiber having an inner core component and an outer sheath component where the inner core component has a higher melting point than the outer sheath component. The ability of the sheath to melt during thermal bonding gives the fiber a heat fusible characteristic. The fiber itself is typically hydrophobic, but can be made hydrophilic by incorporating a surfactant into the sheath of the bicomponent fiber and/or by treating the external surface of the sheath with a surfactant. Exemplary bicomponent fibers and processes for producing the same are described in European Patent Application No. 0 340 763, published Nov. 8, 1989 in the name of Hansen et al. Exemplary acquisition layers having bicomponent fibers are described in U.S. Pat. No. 5,231,122 issued to Palumbo et al. on Jul. 27, 1993; and in International Publication Number WO 94/28838, published Dec. 22, 1994 in the name of Palumbo, et al., each of which is incorporated herein by reference.

The fibrous acquisition layer 25 may comprise a composite of bicomponent fibers and other fibers such as rayon, monocomponent synthetic fibers, and tricomponent synthetic fibers. For example, the fibrous acquisition layer 25 may comprise a blend of 75% bicomponent fibers and 25% rayon fibers.

The fibrous acquisition layer 25 should have an operable level of density and basis weight to rapidly acquire and then drain liquid surges into the underlying absorbent core 24, thus remaining relatively empty to receive subsequent liquid surges. The fibrous acquisition layer 25 should have sufficient void volume capacity to temporarily retain the amount of liquid that is typically discharged by a wearer during a single insult or surge of liquid into the incontinence pad. Insufficient void volume capacity may result in excessive pooling of liquid against the wearer's skin or excessive run-off of liquid.

The basis weight of the fibrous acquisition layer is preferably within the range of from about 10 to about 300 grams per square meter, more preferably from 20 to about 200 grams per square meter, and most preferably from about 30 to about 60 grams per square meter. The fibrous acquisition layer has a thickness of from about 1 to about 10 mm, more preferably from about 1.5 to about 6 mm, still more preferably from about 1.7 to about 4.5 mm, and most preferably from about 2 to about 4 mm, as measured under a pressure of 2 kPa. The fibrous acquisition layer has a bulkiness of from about 10 $cm^3/g$ to about 100 $cm^3/g$, more preferably a bulkiness of from about 15 $cm^3/g$ to about 65 $cm^3/g$, still more preferably from about 20 $cm^3/g$ to about 60 $cm^3/g$, and most preferably from about 25 $cm^3/g$ to about 55 $cm^3/g$.

The rewet barrier 27 is liquid pervious, permitting liquids to readily penetrate through its thickness. The rewet barrier may be joined with the fibrous acquisition layer and the absorbent core by any of the conventional means for joining webs together such as adhesives, heat bonds, pressure bonds, ultrasonic bonds, dynamic mechanical bonds, or any other suitable attachment means or combinations of these attachment means as are known in the art.

A preferred rewet barrier comprises an apertured, macroscopically expanded, three-dimensional, polymeric web. Apertured macroscopically expanded, three-dimensional, polymeric webs are preferred for the rewet barrier because they are pervious to bodily fluids and yet nonabsorbent and have a reduced tendency to allow liquids to pass back through and rewet the wearer's skin. Thus, the outer cover of the incontinence pad which is in contact with the body remains dry, thereby reducing body soiling and creating a more comfortable feel for the wearer. Suitable apertured, macroscopically expanded, three-dimensional, polymeric webs are described in U.S. Pat. No. 3,929,135, issued to Thompson on Dec. 30, 1975; U.S. Pat. No. 4,324,246 issued to Mullane et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference.

Figure 3:
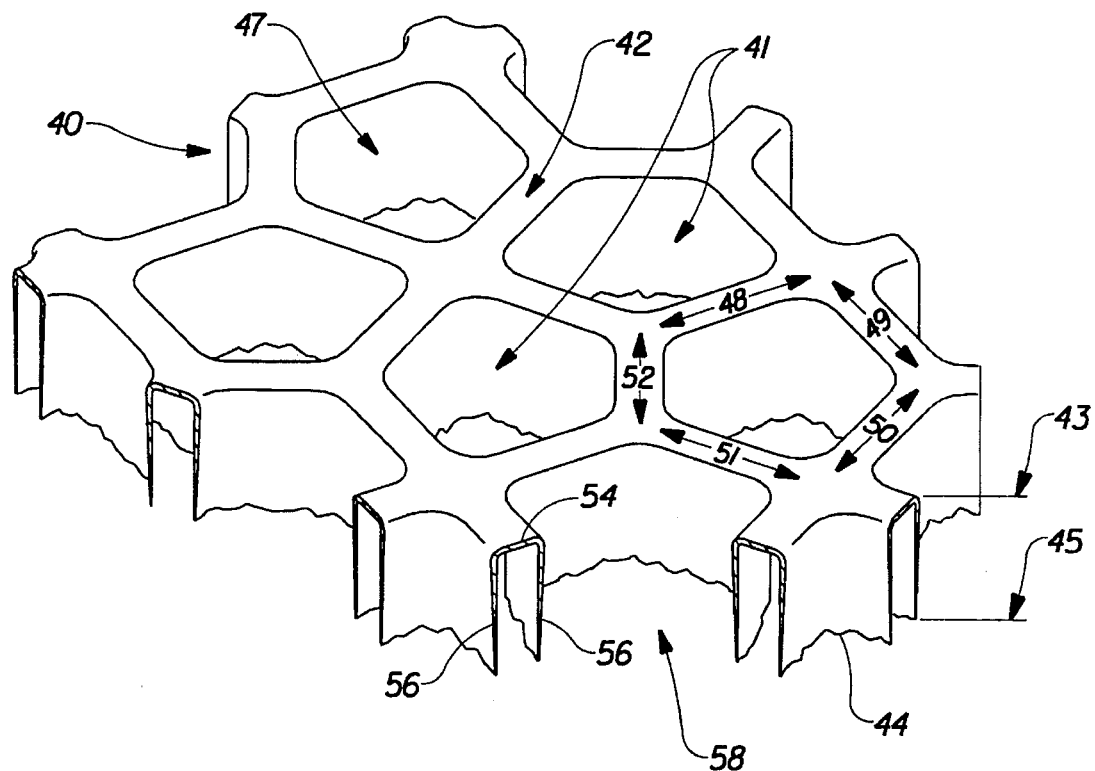
FIG. 3 is an enlarged, partially segmented, perspective illustration of a preferred fluid pervious web suitable for use as the rewet barrier of the present invention.

FIG. 3 is an enlarged, partially segmented, perspective illustration of a particularly preferred embodiment of an apertured, macroscopically expanded, three-dimensional, fiber-like, fluid pervious, polymeric web 40, generally in accordance with the teachings of commonly assigned U.S. Pat. No. 4,342,314 issued to Radel et al. on Aug. 3, 1982, which has been found suitable for use as the rewet barrier 27 on incontinence pad 20. The term "macroscopically expanded", when used to describe three-dimensional plastic webs of the present invention, refers to webs, ribbons and films which have been caused to conform to the surface of a three-dimensional forming structure so that both surfaces thereof exhibit a three-dimensional forming pattern of surface aberrations corresponding to the macroscopic cross-section of the forming structure, the surface aberrations comprising the pattern are individually discernible to the normal naked eye, i.e., a normal naked eye having 20/20 vision unaided by an instrument that changes the apparent size or distance of an object or otherwise alters the visual powers of the eye, when the perpendicular distance between the viewer's eye and the plane of the web is about 12 inches. The term "fiber-like", as utilized herein to describe the appearance of plastic webs of the present invention, refers generally to any fine scale pattern of apertures, random or non random, reticulated or non-reticulated, which connote an overall appearance and impression of a woven or non-woven fibrous web when viewed by the human eye. As can be seen in FIG. 3, the web's fiber-like appearance is comprised of a continuum of fiber-like elements, the opposed ends of each of the fiber-like elements are interconnected to at least one other of the fiber-like elements. In the embodiment disclosed in FIG. 3, the interconnected fiber-like elements form a pattern network of pentagonally shaped capillaries 41. The web 40 which exhibits a fiber-like appearance, embodies a three-dimensional microstructure extending from the web's uppermost, wearer-contacting or body facing surface 42 in plane 43 to its lowermost or garment facing surface 44 in plane 45 to promote rapid fluid transport from the uppermost surface 42 to the lowermost surface 44 of the web without lateral transmission of fluid between adjacent capillaries 41. As utilized herein, the term "microstructure" refers to a structure of such fine scale that its precise detail is readily perceived by the human eye only upon magnification by microscopic or other means well known in the art.

Apertures 47 in the body surface 42 are formed by a multiplicity of intersecting fiber-like elements, e.g., elements 48, 49, 50, 51, and 52, interconnected to one another in the body facing surface of the web. Each fiber-like element comprises a base portion, e.g., base portion 54, located in plane 43. Each base portion has a sidewall portion, e.g., sidewall portions 56, attached to each edge thereof. The sidewall portions 56 extend generally in the direction of the second surface 44 of the web. The intersecting sidewall portions of the fiber-like elements are interconnected to one another intermediate the first and second surfaces of the web and terminate substantially concurrently with one another in the plane 45 of the second surface.

In the embodiment shown in FIG. 3, the interconnected sidewall portions 56 terminate substantially concurrently with one another in the plane of the second surface 45 to form apertures 58 in the second surface 45 of the web. The network of capillaries 41 formed by the interconnected sidewall portions 56 between apertures 47 and 58 allows for free transfer of fluids from the body facing surface of the web directly to the garment facing surface of the web without lateral transmission of the fluid between adjacent capillaries.

The rewet barrier 27 preferably comprises a multilayer polymeric film which exhibits an opaque appearance. The multilayer film includes a first outer layer comprised substantially of a polymeric material and a central filler-containing polymeric layer substantially continuously joined to one side of the first outer layer. The central filler-containing layer preferably has about 20 to 60 weight percent fillers relative to the filler-containing layer which are substantially uniformly dispersed therein. A filler such as titanium dioxide may be used to give the rewet barrier a whitish, opaque appearance. The central filler-containing layer has a thickness from about 30 to about 70 percent of the total thickness of the multilayer film. A second outer layer comprised substantially of a polymeric material has one side substantially continuously joined to the second side of the central filler-containing layer. The total multilayer film preferably has at least 20 weight percent filler relative to the total multilayer film. A suitable example of such a multilayer film is found in commonly assigned U.S. Pat. No. 5,261,099, issued to Visscher and Perry on Nov. 16, 1993 and which is incorporated herein by reference.

Preferred polymeric materials for the outer layers and the central filler containing layer include polyolefins, particularly polyethylenes, polypropylenes and copolymers having at least one olefinic constituent. Other materials such as polyesters, nylons, copolymers thereof and combinations of any foregoing may also be suitable.

In a preferred embodiment of the present invention, the body facing surface of the rewet barrier 27 is hydrophilic so as to help liquid to transfer through the rewet barrier faster than if the rewet barrier was not hydrophilic so as to diminish the likelihood that bodily fluid will flow off the rewet barrier rather than flowing into and being absorbed by the absorbent core. In a preferred embodiment, surfactant is incorporated into the polymeric materials of the rewet barrier such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body facing surface of the rewet barrier can be made hydrophilic by treating it with a surfactant such as is described in the above referenced U.S. Pat. No. 4,950,254 issued to Osborn, incorporated herein by reference.

In use, the incontinence pad 20 can be held in place by any support means or attachment means well-known for such purposes. Preferably, the incontinence pad is placed in the user's undergarment or panty and secured thereto by a fastener such as an adhesive 36. The adhesive 36 provides a means for securing the incontinence pad 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the incontinence pad is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox E 1/0 and BL30MG-A Silox 4P/O both of which are manufactured by the Akrosil Corporation of Menasha, Wisc. The incontinence pad 20 of the present invention is used by removing the release liner 37 and thereafter placing the incontinence pad 20 in a panty so that the adhesive 36 contacts the panty. The adhesive 36 maintains the incontinence pad in its position within the panty during use.

Figure 4:
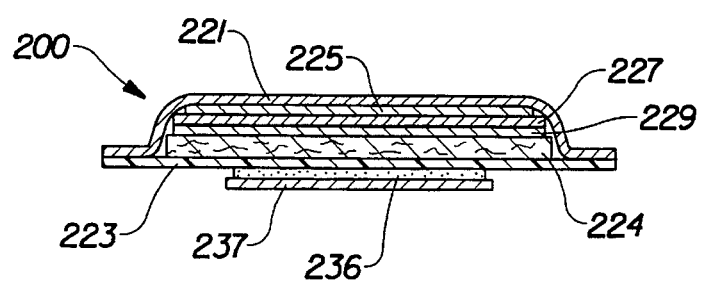
FIG. 4 is a cross-sectional view of another embodiment of an incontinence pad of the present invention.

FIG. 4 is a cross-sectional view of another embodiment of an incontinence pad 200 of the present invention. As shown in FIG. 4, the incontinence pad 200 preferably comprises a liquid pervious topsheet 221, a liquid impervious backsheet 223 joined with the topsheet 221, an absorbent core 224 positioned between the topsheet 221 and the backsheet 223, a first fibrous acquisition layer 225 positioned between the topsheet 221 and the absorbent core 224, a rewet barrier 227 positioned between the first acquisition layer 225 and the absorbent core 224, and a second fibrous acquisition layer 229 positioned between the rewet barrier 227 and the absorbent core 224. The incontinence pad 200 preferably includes an adhesive fastening means 236 for attaching the incontinence pad 200 to the undergarment of the wearer. Removable release liners 237 cover the adhesive fastening means 236 to keep the adhesive from sticking to a surface other than a crotch portion of the undergarment prior to use.

The topsheet 221, backsheet 223, absorbent core 224, rewet barrier 227, adhesive fastening means 236, and release liner 237 of incontinence pad 200 are substantially identical to corresponding features and elements of incontinence pad 20 described above. Accordingly, the discussion of incontinence pad 200 does not contain redundant descriptions of elements and features substantially identical to the elements and features of incontinence pad 20.

The first and second fibrous acquisition layers 225, 229 can be of any desired shape. Suitable shapes include for example, circular, rectangular, triangular, trapezoidal, oblong, dog bone, hourglass, oval, asymmetric, etc. The first and second fibrous acquisition layers 225, 229 may be of any desired dimension. The first and second acquisition layers 225, 229 may have length and width dimensions larger than, greater than, or equal to those of the rewet barrier 227. Further, the first and second acquisition layers 225, 229 may have length and width dimensions larger than, greater than, or equal to each other.

The first and second fibrous acquisition layers 225, 229 may serve several functions including accepting a high rate of fluid intake, serving as a temporary reservoir for the fluid, improving the wicking of fluids over and into the absorbent core, and draining substantially completely into the absorbent core in order to remain empty for subsequent fluid loadings. There are several reasons why the improved wicking of bodily fluids is important, including providing a more even distribution of the bodily fluids throughout the absorbent core. The wicking referred to herein may encompass the transportation of liquids in one, two, or all directions (i.e., in the x-y plane and/or in the z-direction). In addition, this element must resist collapse when wet so that it maintains its performance through multiple loadings. This element must do all these things while also remaining thin.

The first and second fibrous acquisition layers 225, 229 may be comprised of several different materials including nonwoven or woven webs of synthetic fibers including polyester, polypropylene, or polyethylene; natural fibers including cotton or cellulose; blends of such fibers; or any equivalent materials or combinations of materials. Suitable nonwoven webs include bonded carded webs, spunbonded webs, thermally bonded airlaid webs, and meltblown webs. The acquisition layers may be joined with the other components, such as the topsheet, the rewet barrier, and the absorbent core, by any of the conventional means for joining webs together such as adhesives, heat bonds, pressure bonds, ultrasonic bonds, dynamic mechanical bonds, or any other suitable attachment means or combinations of these attachment means as are known in the art.

If the fibrous acquisition layers comprise a nonwoven web, the nonwoven web may be a spunbonded web, a meltblown web, a bonded carded web or a thermally bonded airlaid web. The nonwoven web may be made of fiber forming polymers such as, for example, polyesters, polyamines, and polyolefins. Exemplary polyolefins include one or more of polypropylene, polyethylene, ethylene copolymers, propylene copolymers, and butene copolymers. In another embodiment, the acquisition layers may be a multi-layer material having, for example, at least one layer of a spunbonded web joined to at least one layer of a meltblown web, a bonded carded web, a thermally bonded airlaid web, or other suitable material. Alternatively, the nonwoven web may be a single layer of material such as, for example, a spunbonded web or a meltblown web.

The nonwoven web may also be a composite made up of a mixture of two or more different fibers or a mixture of fibers and particles. Such mixtures may be formed by adding fibers and/or particulates to the gas stream in which the meltblown fibers or spunbonded fibers are carried so that an intimate entangled commingling of fibers and other materials, e.g., wood pulp, staple fibers, superabsorbent materials, and particles occurs prior to collection of the fibers.

In another preferred embodiment, the nonwoven web may be comprised of bicomponent fibers. The bicomponent fiber is preferably a thermobondable bicomponent fiber having an inner core component and an outer sheath component where the inner core component has a higher melting point than the outer sheath component. The ability of the sheath to melt during thermal bonding gives the fiber a heat fusible characteristic. The fiber itself is typically hydrophobic, but can be made hydrophilic by incorporating a surfactant into the sheath of the bicomponent fiber and/or by treating the external surface of the sheath with a surfactant. Suitable acquisition layers having bicomponent fibers are described in U.S. Pat. No. 5,231,122 issued to Palumbo et al. on Jul. 27, 1993, which is incorporated herein by reference.

The first fibrous acquisition layer 225 should have an operable level of density and basis weight to rapidly acquire and then drain liquid surges through the rewet barrier 227 and into the underlying second fibrous acquisition layer 229, thus remaining relatively empty to receive subsequent liquid surges. The first fibrous acquisition layer 225 should have sufficient void volume capacity to temporarily retain the amount of liquid that is typically discharged by a wearer during a single insult or surge of liquid into the incontinence pad. However, there may be instances when the incontinence pad 200 is subjected to larger liquid surges or multiple liquid surges which exceed the void volume capacity of the first fibrous acquisition layer 225.

The second fibrous acquisition layer 229 provides additional void volume capacity to enable the incontinence pad 200 to handle larger liquid surges or multiple liquid surges which exceed the void volume capacity of the first fibrous acquisition layer 225. Thus, the first and second fibrous acquisition layers 225, 229 together provide a sufficient void volume capacity to reduce the risk of excessive pooling of liquid against the wearer's skin or excessive run-off of liquid.

The first and second fibrous acquisition layers 225, 229 may be identical to or different from one another. For example, in some embodiments it may be desirable to construct the incontinence pad 200 such that the second fibrous acquisition layer 229 has an effective average pore size which is greater than the effective average pore size of the first fibrous acquisition layer 225 to provide the incontinence pad with a gradient for improved acquisition. Additionally, the first fibrous acquisition layer may comprise a fiber composition different from the second fibrous acquisition layer. For example, the first fibrous acquisition layer may comprise 100% bicomponent fibers and the second fibrous acquisition layer may comprise a blend of bicomponent fibers and other fibers such as rayon, monocomponent fibers, and tri-component fibers.

The basis weight of the first fibrous acquisition layer 225 is preferably within the range of from about 10 to about 300 grams per square meter, more preferably from 20 to about 200 grams per square meter, and most preferably from about 30 to about 60 grams per square meter. The first fibrous acquisition layer has a thickness of from about 1 to about 10 mm, more preferably from about 1.5 to about 6 mm, still more preferably from about 1.7 to about 4.5 mm, and most preferably from about 2 to about 4 mm, as measured under a pressure of 2 kPa. The first fibrous acquisition layer has a bulkiness of from about 10 $cm^3/g$ to about 100 $cm^3/g$, more preferably a bulkiness of from about 15 $cm^3/g$ to about 65 $cm^3/g$, still more preferably from about 20 $cm^3/g$ to about 60 $cm^3/g$, and most preferably from about 25 $cm^3/g$ to about 55 $cm^3/g$.

The basis weight of the second fibrous acquisition layer 229 is preferably within the range of from about 10 to about 300 grams per square meter, more preferably from 20 to about 200 grams per square meter, and most preferably from about 30 to about 60 grams per square meter. The second fibrous acquisition layer has a thickness of from about 1 to about 10 mm, more preferably from about 1.5 to about 6 mm, still more preferably from about 1.7 to about 4.5 mm, and most preferably from about 2 to about 4 mm, as measured under a pressure of 2 kPa. The second fibrous acquisition layer has a bulkiness of from about 10 $cm^3/g$ to about 100 $cm^3/g$, more preferably a bulkiness of from about 15 $cm^3/g$ to about 65 $cm^3/g$, still more preferably from about 20 $cm^3/g$ to about 60 $cm^3/g$, and most preferably from about 25 $cm^3/g$ to about 55 $cm^3/g$.

In an alternative embodiment the incontinence pad 200 may contain an additional rewet barrier comprising an apertured, macroscopically expanded, three-dimensional, polymeric web positioned between the topsheet 221 and the first fibrous acquisition layer 225. The additional rewet barrier will help to further minimize the risk of liquid passing back through and rewetting the wearer's skin.

In another embodiment the incontinence pad 200 may comprise an additional fluid distribution layer positioned between the topsheet 221 and the first fibrous acquisition layer 225. The fluid distribution layer will help to further distribute fluid in the longitudinal and transverse directions to better utilize the void volume capacity of the underlying first fibrous acquisition layer 225. The fluid distribution layer may be made from several different materials including nonwoven or woven webs of synthetic fibers including polyester, polypropylene, or polyethylene; natural fibers including cotton or cellulose; blends of such fibers; or any equivalent materials or combinations of materials. Suitable nonwoven webs include bonded carded webs, spunbonded webs, meltblown webs, and thermally bonded airlaid webs.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

(a) a liquid pervious topsheet;

(b) a liquid impervious backsheet joined to said topsheet;

(c) an absorbent core positioned between said topsheet and said backsheet;

(d) a first fibrous acquisition layer positioned between said topsheet and said absorbent core;

(e) a rewet barrier positioned between said fibrous acquisition layer and said absorbent core, said rewet barrier comprising an apertured, macroscopically expanded, three-dimensional, polymeric web having a body facing surface and a garment facing surface; and (f) a second fibrous acquisition layer positioned between said rewet barrier and said absorbent core.

2. The absorbent article of claim 1 wherein said first and second fibrous acquisition layers are nonwoven webs selected from the group consisting of a bonded carded web of fibers, a web of spunbonded fibers, a web of meltblown fibers, a web of thermally bonded airlaid fibers, and a multilayer material including at least one of said webs.

3. The absorbent article of claim 2 wherein said fibers comprise a polymer selected from the group consisting of polyolefins, polyesters, and polyamines.

4. The absorbent article of claim 1 wherein said first and second fibrous acquisition layers are comprised of bicomponent fibers.

5. The absorbent article of claim 1 wherein said first and second fibrous acquisition layers are composites comprising a mixture of bicomponent fibers and one or more other fibers selected from the group consisting of rayon, monocomponent fibers, and tri-component fibers.

6. The absorbent article of claim 1 wherein said first fibrous acquisition layer is a nonwoven web selected from the group consisting of a bonded carded web of fibers, a web of spunbonded fibers, a web of meltblown fibers, a web of thermally bonded airlaid fibers, and a multilayer material including at least one of said webs.

7. The absorbent article of claim 6 wherein said fibers comprise a polymer selected from the group consisting of polyolefins, polyesters, and polyamines.

8. The absorbent article of claim 6 wherein said nonwoven web is a composite material comprising a mixture of fibers and one or more other materials selected from the group consisting of wood pulp, staple fibers, particulates and superabsorbent materials.

9. The absorbent article of claim 1 wherein the body facing surface of the rewet barrier is located in a first plane and the garment facing surface of the rewet barrier is located in a second plane remote from said first plane.

10. The absorbent article of claim 1 wherein said first fibrous acquisition layer is comprised of bicomponent fibers.

11. The absorbent article of claim 1 wherein said first fibrous acquisition layer is a composite comprising a mixture of bicomponent fibers and one or more other fibers selected from the group consisting of rayon, monocomponent fibers, and tri-component fibers.

12. The absorbent article of claim 1 wherein said second fibrous acquisition layer is a nonwoven web selected from the group consisting of a bonded carded web of fibers, a web of spunbonded fibers, a web of meltblown fibers, a web of thermally bonded airlaid fibers, and a multilayer material including at least one of said webs.

13. The absorbent article of claim 12 wherein said fibers comprise a polymer selected from the group consisting of polyolefins, polyesters, and polyamines.

14. The absorbent article of claim 12 wherein said nonwoven web is a composite material comprising a mixture of fibers and one or more other materials selected from the group consisting of wood pulp, staple fibers, particulates and superabsorbent materials.

15. The absorbent article of claim 1 wherein said second fibrous acquisition layer is comprised of bicomponent fibers.

16. The absorbent article of claim 1 wherein said second fibrous acquisition layer is a composite comprising a mixture of bicomponent fibers and one or more other fibers selected from the group consisting of rayon, monocomponent fibers, and tri-component fibers.

* * * * *